United States Patent
Silverberg et al.

[11] Patent Number: 6,100,435
[45] Date of Patent: Aug. 8, 2000

[54] USE OF CATALYTIC DISTILLATION TO PRODUCE CYCLOPENTANE OR CYCLOPENTENE

[75] Inventors: Steven E. Silverberg, Seabrook, Tex.; Leonel E. Sanchez, Guatemala City, Guatemala; James R. Lattner, Seabrook, Tex.

[73] Assignee: Exxon Chemical Patents Inc., Houston, Tex.

[21] Appl. No.: 09/191,488

[22] Filed: Nov. 13, 1998

[51] Int. Cl.$^7$ .............. C07C 1/00; C07C 4/22; C07C 13/15; C07C 5/33
[52] U.S. Cl. ............ 585/318; 585/317; 585/256; 585/354; 203/DIG. 6
[58] Field of Search .................... 585/317, 318, 585/256, 354; 203/DIG. 6

[56] References Cited

U.S. PATENT DOCUMENTS

| | | | |
|---|---|---|---|
| 2,407,214 | 9/1946 | Birch et al. | 260/566 |
| 2,420,030 | 5/1947 | Brandon | 196/61 |
| 2,887,517 | 5/1959 | Noeske et al. | 260/666 |
| 3,598,877 | 8/1971 | Fountain et al. | 260/666 A |
| 3,763,254 | 10/1973 | Engelhard et al. | 260/666 A |
| 3,788,979 | 1/1974 | Caflisch et al. | 208/255 |
| 3,998,897 | 12/1976 | Kovach et al. | 260/666 A |
| 4,194,964 | 3/1980 | Chen et al. | 208/108 |
| 4,213,847 | 7/1980 | Chen et al. | 208/111 |
| 5,258,560 | 11/1993 | Marker | 568/697 |
| 5,284,987 | 2/1994 | Sikkenga et al. | 585/410 |
| 5,308,592 | 5/1994 | Yang et al. | 422/191 |
| 5,321,181 | 6/1994 | Smith, Jr. et al. | 585/467 |
| 5,362,377 | 11/1994 | Marker | 208/133 |
| 5,463,156 | 10/1995 | Muroi et al. | 585/400 |
| 5,498,318 | 3/1996 | Alagy et al. | 203/29 |

FOREIGN PATENT DOCUMENTS

| | | |
|---|---|---|
| 2 271 575 | 4/1994 | United Kingdom . |
| 2 273 107 | 6/1994 | United Kingdom . |

*Primary Examiner*—Walter D. Griffin
*Assistant Examiner*—Thuan D. Dang

[57] ABSTRACT

A process is disclosed for converting dicyclopentadiene to cyclopentane and/or cyclopentene, wherein dicyclopentadiene is fed to a catalytic distillation column, the dicyclopentadiene is cracked to cyclopentadiene in the catalytic distillation column, the cyclopentadiene is hydrogenated to cyclopentane in the catalytic distillation column, and the cyclopentane is recovered from the catalytic distillation column. The dicyclopentadiene is fed into and cracked to cyclopentadiene at the bottom of the catalytic distillation column. Hydrogen is then fed to the catalytic distillation column below the catalytic zone, where cyclopentadiene is hydrogenated as it is produced, thus suppressing polymerization of the cyclopentadiene. The resulting cyclopentane and/or cyclopentene vapor phase stream is condensed, thereby producing a liquid stream of cyclopentane and/or cyclopentene and a vapor stream of hydrogen and other off-gas by-products.

17 Claims, 2 Drawing Sheets

USE OF CATALYTIC DISTILLATION TO PRODUCE CYCLOPENTANE OR CYCLOPENTENE

The present invention relates generally to the production of cyclopentane or cyclopentene by catalytic distillation. In particular, it relates to the production of cyclopentane liquid distillate from dicyclopentadiene, wherein a single catalytic distillation column replaces the hydrotreating unit and two distillation columns that are used in known processes for production of cyclopentane.

BACKGROUND OF THE INVENTION

Cyclopentane, a solvent and blowing agent having a basic formula of $C_5H_{10}$, is typically produced in a two column and hydrotreating unit system. The conventional process for production of cyclopentane includes: (1) cracking dicyclopentadiene (DCPD) in a distillation column or other reaction vessel; (2) recovering cyclopentadiene (CPD) as liquid distillate from the distillation column; and (3) hydrogenating CPD in a hydrotreating unit. The resulting product is fed to a cyclopentane recovery column wherein cyclopentane (CYC5) is recovered as a liquid distillate. This process is characterized by the following primary reactions:

DCPD→2 CPD

CPD+$H_2$→$C_5H_8$ $C_5H_8$+$H_2$→CYC5

Part of the CYC5 may be sent to the first reactive distillation column to be used as a diluent to minimize CPD polymerization reaction in the upper section of the column.

This process requires a hydrotreating unit and two distillation columns, as shown in FIG. 1. FIG. 1 depicts a standard hydrogenation process employed in the art. This prior art process for the formation of CYC5 employs a multicomponent system generally referred to by reference numeral 10. System 10 includes hydrotreating unit 12, first distillation column 14 and second distillation column 16. First distillation column 14, hydrotreating unit 12, and second distillation column 16 are linked in series by conduits 61 and 20, respectively.

Initially, DCPD is fed via conduit 22 into first distillation column 14, where it is cracked according to the following reaction:

DCPD→2 CPD

Preferred distillation conditions are a temperature of about 465° F. (240° C.) and a pressure of 8 psig (0.16 MPa). The resulting CPD is recovered as an overhead vapor stream and heavies are taken as bottoms via conduit 58. These heavy by-products can be removed from system 10 via conduit 59 or can be recycled through reboiler 66 to the bottom section of distillation column 14. The overhead vapor stream is transferred to condenser 54 via conduit 18. The CPD condensate is taken from condenser 54 via conduit 55, where it is either recycled to the top portion of distillation column 14 via conduit 57 as a diluent to minimize CPD polymerization reaction in the upper section of the column or to hydrotreating unit 12 via conduit 61 for further hydrogenation.

Hydrogen is fed via conduit 24 into hydrotreating unit 12, preferably in the form of $H_2$ gas, such that it comes into contact with the CPD received via conduit 61. The CPD is then hydrogenated to CYC5 in hydrotreating unit 12 according to the reaction set forth below:

CPD+2$H_2$→CYC5

This reaction is typically carried out at an elevated operating pressure (i.e.,>200 psig). Following the reaction, various separation steps are necessary to disengage the unreacted $H_2$ from the hydrocarbon product. The resulting product is then transferred to second distillation column 16 via conduit 20. In second distillation column 16, CYC5 is recovered as a liquid distillate, and part or all of the CYC5 liquid distillate is removed overhead via conduit 60. Optionally, a portion of the CYC5 liquid distillate or a portion of the liquid from conduit 20 may be recycled to first distillation column 14 via conduit 62 to be used as a diluent (alone or in conjunction with liquid CPD) to minimize CPD polymerization reaction in the upper section of column 14 and to control the temperature increase in hydrogenation. Heavy by-products are removed as bottoms from second distillation column 16 via conduit 64. As such, substantial operating costs are incurred to maintain the three distinct reaction vessels. In addition, initial capital costs are high, and processing times are extended.

Conventional processes for the production of cyclopentene (with cyclopentane produced and recycled as an impurity) from dicyclopentadiene are disclosed in U.S. Pat. No. 4,048,242 (Lauer et al.). The Lauer et al. patent discloses a multi-vessel reaction process that is subject to the same cost and time limitations as the foregoing prior art process.

British patent application GB-A-2273017 (commonly owned with the present application) discloses the manufacture of cyclopentane from dicyclopentadiene by cracking the dimer in a heat exchanger and hydrogenating the monomer to form cyclopentane in a closed loop batch reactor at a temperature below 175° C. The effluent is then fed to a flash drum separator and to a distillation column and fractionation column [pp. 10–11].

British patent application GB-A-2271575 (also commonly owned with the present application) discloses the production of cyclopentane from dicycloalkadiene by similar methods, wherein cyclopentane is added as a diluent in the manufacture of additional cyclopentane.

Accordingly, a need exists for an improved, simplified, more efficient process for the production of cyclopentane.

It has been suggested in the past to apply catalytic distillation to a wide variety of processes such as butene isomerization (see U.S. Pat. No. 2,403,672 to M. P. Matuzak); the hydrolysis of low molecular weight olefin oxides to produce mono-alkylene glycols (see U.S. Pat. No. 2,839,588 to A. S. Parker); and the production of methyl tertiary butyl ether (MTBE) (see U.S. Pat. No. 3,634,535 to W. Haunschild). Catalytic distillation is only now emerging as a commercially viable hydrocarbon conversion and petrochemical processing tool.

Advantages attributed to the catalytic distillation concept, wherein reaction products are continuously separated from the reactants and removed from the reaction zone by fractional distillation performed concurrently with the reaction, include a decrease in the capital cost of the plant needed to perform the process, the ability to achieve a higher degree of conversion, and the ability to perform processes which formerly were performed only in a batch type operation on a continuous basis. These advantages result from performing the reaction in a separation zone capable of removing the reaction products from the reactants and catalyst. Hence, it is only necessary to provide one primary vessel and the reaction is not limited by chemical equilibrium.

A further advantage of the catalytic distillation process is that there is no need for a high pressure hydrogenation step and all the increased capital and processing costs associated therewith.

The present inventor has developed a unique one step process which is capable of producing a high yield of cyclopentane with high selectivity in a single catalytic distillation column. This process also avoids the need to recycle product as diluent to minimize CPD polymerization reaction.

Other and further objects, advantages and features of the present invention will be understood by reference to the following specification in conjunction with the annexed drawings.

SUMMARY OF THE INVENTION

A process is disclosed for converting dicyclopentadiene to cyclopentane, wherein dicyclopentadiene is fed to a catalytic distillation column, the dicyclopentadiene is cracked to cyclopentadiene in the catalytic distillation column, the cyclopentadiene is hydrogenated to cyclopentane in the catalytic distillation column, and the cyclopentane is recovered as a liquid condensate overhead from the catalytic distillation column. The dicyclopentadiene is fed into and cracked to cyclopentadiene at the bottom portion of the catalytic distillation column from which it vaporizes and flows upward. Hydrogen is then fed to the catalytic distillation column below the catalytic zone, where cyclopentadiene is hydrogenated as it is produced, thus suppressing polymerization of the cyclopentadiene. The resulting cyclopentane vapor phase stream is condensed, thereby producing a liquid stream of cyclopentane and a vapor stream of hydrogen and other off-gas by-products.

A process is also disclosed for converting dicyclopentadiene to cyclopentene. While the process of the present invention is primarily referred to in the context of cyclopentane production, cyclopentene can be made by a similar process, differing from the process for production of cyclopentane only in that the hydrogenation process is controlled to convert cyclopentadiene into cyclopentene, instead of cyclopentane, by methods known in the art, such as by restricting the hydrogen treatgas rate to the stoichiometric ratio.

The processes of the present invention are streamlined and cost-efficient, providing both capital and operating cost savings. Moreover, high selectivity can be achieved with the single-component system of this invention.

DESCRIPTION OF THE PREFERRED EMBODIMENTS

Figure 1:
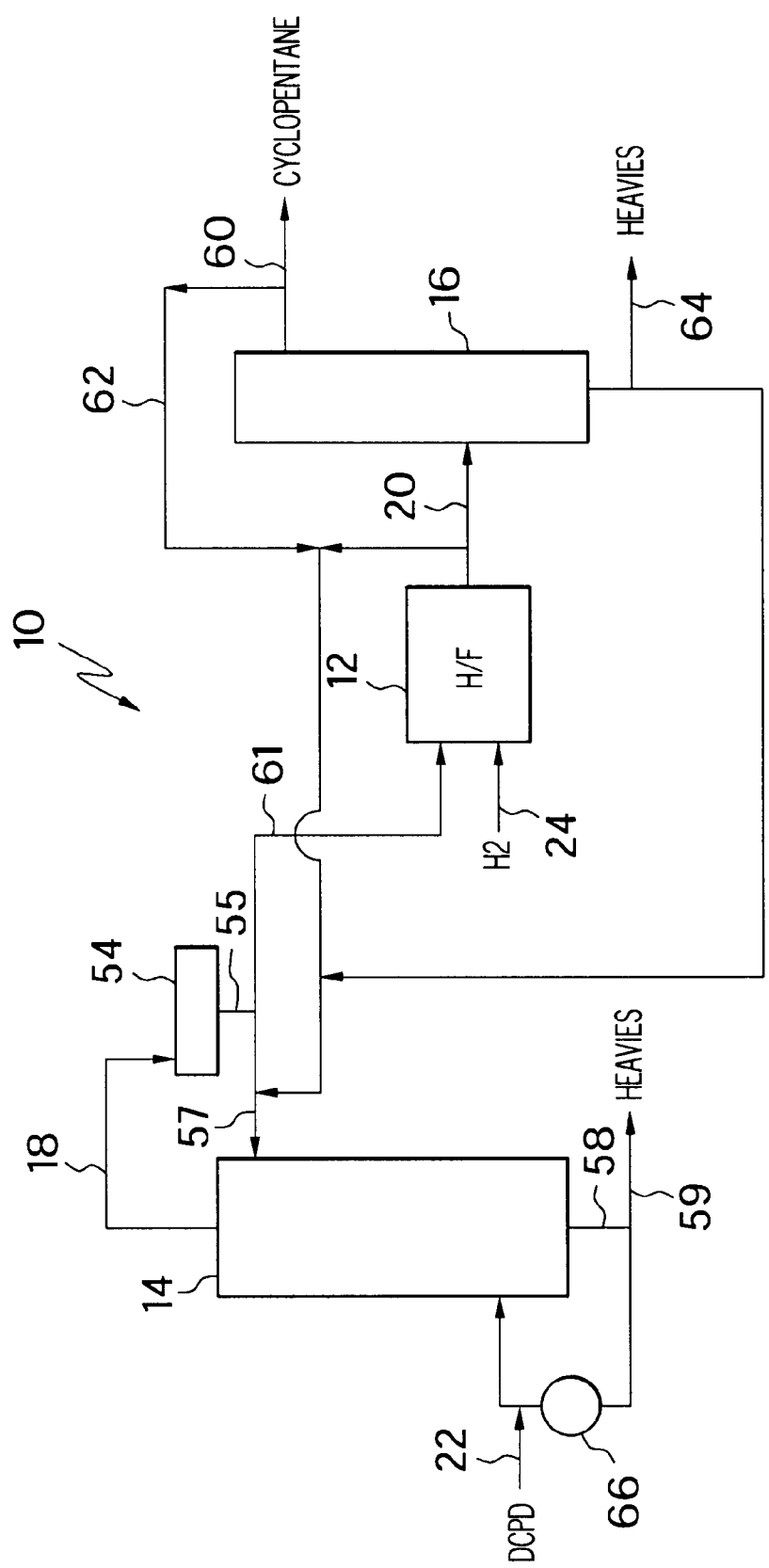
FIG. 1 (discussed above) is a schematic representation of the prior art process wherein DCPD is converted to CYC5 in a two distillation column and hydrotreating unit system.
Figure 2:
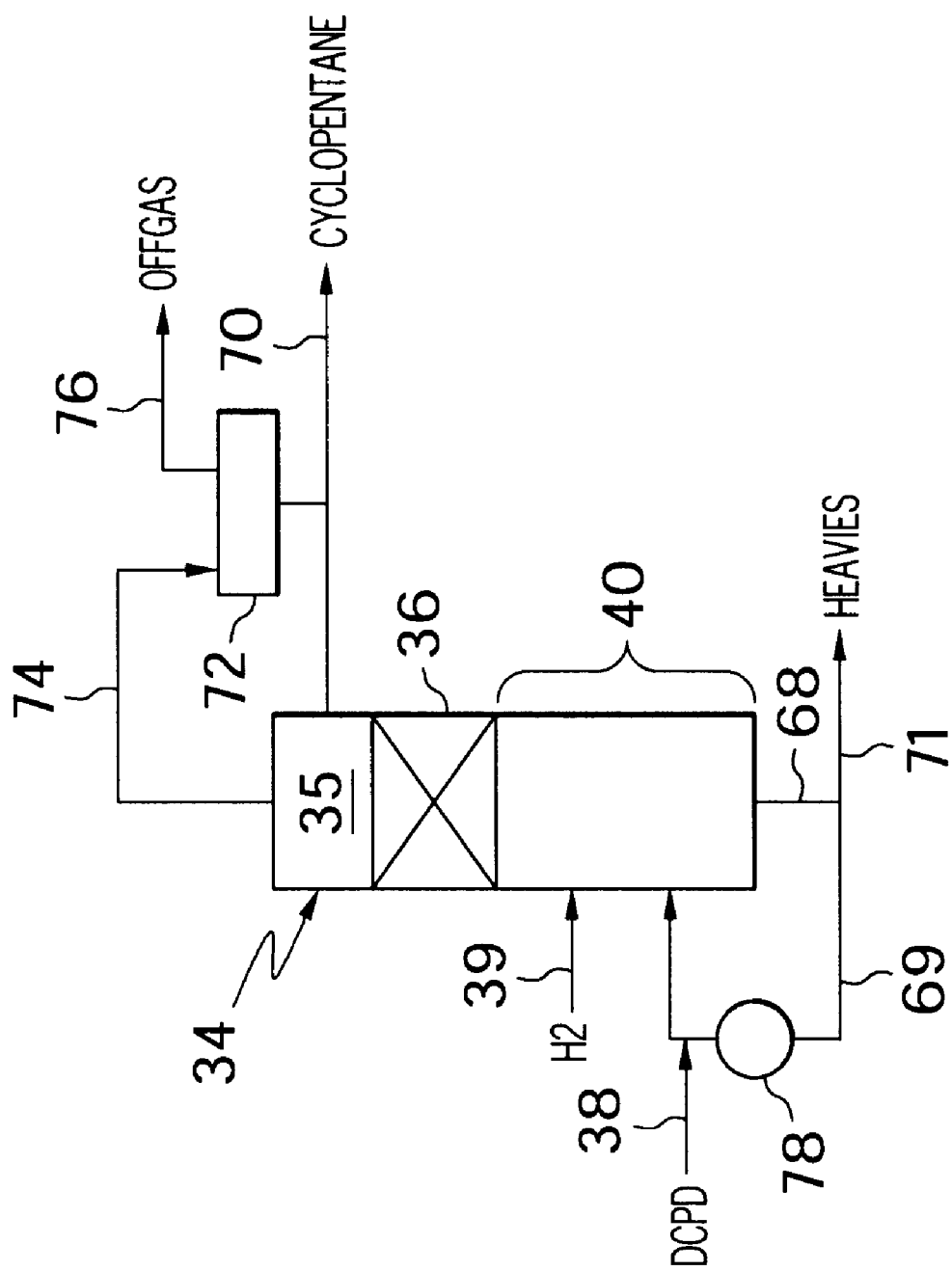
FIG. 2 is a schematic representation of the process according to a preferred embodiment of the present invention wherein CYC5 is produced by: 1) DCPD cracking to CPD; 2) hydrogenation of CPD to either CYC5 or cyclopentene; and 3) distillation to separate out the desired product; all in a single catalytic distillation column.

A preferred embodiment according to the present invention is depicted in FIG. 2. Instead of the three-component system of the prior art, the present invention requires only a single catalytic distillation column, generally referred to in FIG. 2 by reference numeral 34. Catalytic distillation column 34 includes catalytic zone 36, preferably situated in a middle or upper portion of catalytic distillation column 34.

Catalytic zone 36 preferably includes a known heterogeneous hydrogenation catalyst consisting of a metal on a support. Catalyst supports may include alumina, silica alumina, carbon or others. Catalytic metals may include massive nickel, nickel-molybdenum, cobalt molybdenum, platinum, palladium, and copper chromite, among others. The catalyst is typically in the shape of a $\frac{1}{32}$" long cylinder although other shapes and sizes of catalyst particles may be used. These catalyst particles are held in the reaction zone by structured packing which is designed both to retain the catalyst particles and to provide effective contact in the reaction zone between vapor, liquid and catalyst. This contacting enables simultaneous reaction and separation by distillation to occur in this zone.

Catalytic distillation column 34 may preferably contain: a lower fractionation zone (or bottom cracking zone) 40 having multiple vapor-liquid contacting trays, a central catalytic zone 36 having one or more catalyst beds in packing structure, and an upper fractionation zone (or top distillation zone) 35 having one or more fractionation or equilibrium trays, e.g. approximately ten theoretical trays. The use of approximately one to five vapor-liquid contacting trays is preferred in the bottom cracking zone 40. In a distillation column, such as catalytic distillation column 34, equilibrium exists between gas and liquid throughout the length of the column. In addition, the column is preferably operated at a temperature in the range between about 50 to 350° C., most preferably at about 240° C. (465° F.) bottom temperature, and at a pressure between full vacuum and about 50 psig, most preferably at about 8 psig. Because the reaction product is continuously being separated from the reactants by fractional distillation in catalytic distillation column 34, the process can run on a continuous basis instead of a batch-type basis. Thus, the reaction is not curtailed by reaching chemical equilibrium.

DCPD is fed into catalytic distillation column 34 via conduit 38 along with up to 20% of a diluent solvent, and preferably enters catalytic distillation column 34 at a location below catalytic zone 36. DCPD is cracked to CPD within the bottom cracking zone 40 or reboiler 78 of catalytic distillation column 34. Hydrogen, preferably in the form of $H_2$ gas, is also fed into catalytic distillation column 34 via conduit 39. It is preferred that the hydrogen gas also be fed into catalytic distillation column 34 at a location below catalytic zone 36. Vapor phase CPD, produced by cracking from DCPD, is then hydrogenated in the presence of the hydrogen gas and in the presence of a hydrogenation catalyst in catalytic zone 36 to form CYC5. The vapor phase CPD is diluted by saturated liquid flowing down the column and hydrogenated as it is produced in catalytic distillation column 34, thus suppressing a CPD polymerization reaction, which would otherwise occur according to the prior art reactions set forth above. The resulting CYC5 is selectively distilled as a vapor phase away from catalytic zone 36 as it is formed. The CYC5 vapor phase can be taken as a side stream 70 from a top distillation portion 35 of column 34, or can be taken overhead to condenser 72 via conduit 74 for further concentration before being released to conduit 70. Unreacted treatgas, including hydrogen and any other treatgas impurities (e.g., methane or ethane) is removed overhead from condenser 72 as an offgas via conduit 76. Heavy by-products are taken as bottoms via conduit 68, and can be recycled to the cracking zone 40 via conduit 69 and reboiler 78. Alternatively, these heavies can be purged from the system via conduit 71.

The pressure in condenser 72 is controlled such that the tower overhead pressure in the bottom section of column 34 is set at a predetermined level (e.g. 8 psig) but is not independently controlled. Maintaining a minimum tower overhead pressure reduces the likelihood of CPD reversion to DCPD while still allowing cyclopentane condensation with normally available cooling water rather than a costly refrigeration system. In addition, minimum column pressure drop in column 34 is desirable to allow a minimum pressure to be established in the bottom section thereof. On the other hand, a sufficient pressure drop is necessary for adequate functioning of the vapor-liquid contacting devices.

Column 34 bottoms temperature is preferably set at approximately 465° F. or greater. These temperatures are preferable to achieve high conversion of DCPD to CPD at the pressure induced by the selected tower overhead pressure.

The preferred residence time of liquid in the tower bottoms circuit is approximately fifteen minutes to two hours, most preferably one hour or greater, based on the preferred bottoms liquid draw-off rate.

DCPD diluent is a hydrocarbon which is of sufficiently low volatility to avoid any vaporization at the desired bottoms operating temperature and sufficiently high solvency to preclude polymer buildup in the reboiler 78. The preferred diluent to DCPD ratio is from about 0:100 to about 90:10, with a more preferred ratio from about 5:95 to 20:80, and a most preferred ratio of about 10:90. This diluent is preferably a heavy fraction with a flash point of greater than about 200° F. (93° C.), such as a kerosene fraction. The preferred DCPD for this process is a commercially traded 50–100% purity grade, more preferably an 80–95% purity grade. Acceptable feed concentration is up to about 100% DCPD. The process enables the production of a cyclopentane product of about 97–98% purity from the preferred feed.

The approximate temperature in the reaction zone consistent with approximately an 8 psig (0.156 MPa) overhead pressure, approximately a 465° F. (240° C.) bottoms temperature, and a recovery of a high purity cyclopentane liquid distillate, is between about 100 to 400° F. (38 to 204° C.), preferably about 150–200° F. (65 to 93° C.), and most preferably about 175° F. (79° C.). Lower temperatures are believed to result in some fouling due to polymerization of ligand reactants.

The preferred reflux to distillate ratio is about 0.5–2.0, preferably about 1.0 or less. The preferred hydrogen treatgas rate is more than 100% up to about 150% of stoichiometric requirements for full conversion to cyclopentane. Cyclopentene is produced by restricting treatgas rate to the stoichiometric ratio.

The demonstrated weight hourly space velocity, relating hourly cyclopentane production to amount of catalyst used, is about 0.08 pounds/hour per pound of catalyst. Preferably, the space velocity is higher.

The preferred DCPD for this process is the commercially traded 80–90% purity grade. The acceptable feed concentration is up to about 100% DCPD. The process allows manufacturing a cycloproduct product at least 95% pure, preferably about 97–98% pure, from the preferred feed.

The following experimental data demonstrate the operating parameters of the present invention versus those of the prior art.

| | CYCLOPENTANE | |
|---|---|---|
| | Conventional Hydrogenation | Catalytic Distillation |
| Pressure (psig) | 200 and up | 8 |
| Temperature (° F.) | 200–450 (adiabatic) | 175 (isothermal) |
| Catalyst | Massive nickel hydrogenation catalyst | Massive nickel hydrogenation catalyst |
| WHSV (weight hourly space velocity-lb/hour/lb of catalyst) | ≦0.15 | 0.08 (CYC5) |
| Treatgas Ratio (hydrogen to feed ratio) | >1000 SCF/Bbl | 150% of stoichiometric |
| Reflux Ratio (R/D) | — | 1.0 |
| Conversion | >99% | >99% |

The processes of the present invention provide the unexpected result of being able to hydrogenate at low pressures, i.e., 8 psig, in a catalytic distillation reactor, versus normal hydrogenation processes which operate at pressures of 200 to 3,000 psig. In turn, lower capital costs are required to set up these low pressure systems. Furthermore, reduced energy costs are required to operate these low pressure systems. Typical operating temperatures will be consistent with standard distillation temperatures.

The invention having been thus described with particular reference to the preferred forms thereof, it will be obvious that various changes and modifications may be made therein without departing from the spirit and scope of the invention as defined in the appended claims.

What is claimed is:

1. A process for converting dicyclopentadiene to cyclopentane and/or cyclopentene, wherein said process comprises:

(a) feeding said dicyclopentadiene to a catalytic distillation column;

(b) cracking said dicyclopentadiene to cyclopentadiene in said catalytic distillation column;

(c) hydrogenating said cyclopentadiene to cyclopentane and/or cyclopentene in said catalytic distillation column; and (d) recovering a distillate comprising cyclopentane and/or cyclopentene from said catalytic distillation column.

2. The process of claim 1, wherein said catalytic distillation column comprises an upper hydrogenation and/or distillation zone and a lower cracking and/or separation zone.

3. The process of claim 2, wherein said lower cracking and/or separation zone comprises a location where dicyclopentadiene is cracked to cyclopentadiene, and said cyclopentadiene is vaporized and separated from said dicyclopentadiene.

4. The process of claim 2, wherein said dicyclopentadiene is fed to said lower cracking and/or separation zone.

5. The process of claim 2, wherein said hydrogenation and/or distillation zone comprises a location where cyclopentadiene is hydrogenated to cyclopentane and/or cyclopentene, and said cyclopentane and/or cyclopentene are separated from said cyclopentadiene.

6. The process of claim 2, wherein hydrogen is fed below said upper hydrogenation and/or distillation zone.

7. The process of claim 1, wherein said cyclopentadiene is diluted and hydrogenated as it is produced, thus suppressing polymerization of said cyclopentadiene.

8. The process of claim 1, further comprising the step of condensing an overhead vapor phase stream from said catalytic distillation column, thereby producing a liquid stream comprising cyclopentane and/or cyclopentene and a vapor stream comprising hydrogen and other off-gas by-products.

9. The process of claim 8, wherein said liquid stream is separated from said vapor stream comprising hydrogen and other off-gas by-products.

10. The process of claim 1, wherein about 90% or greater of said dicyclopentadiene that is fed to said catalytic distillation column is converted to said cyclopentane and/or cyclopentene.

11. The process of claim 1, wherein said distillate comprises at least about 90% cyclopentane and/or cyclopentene.

12. The process of claim 1, wherein said catalytic distillation column is operated at a temperature in the range of about 50 to about 350° C.

13. The process of claim 1, wherein said catalytic distillation column is operated at a pressure between about 0 to about 50 psig.

14. The process of claim 1, wherein said catalytic distillation column contains a catalyst selected from the group consisting of massive nickel, nickel-molybdenum, cobalt molybdenum, platinum, palladium, copper chromite and combinations thereof.

15. The process of claim 2, wherein said lower cracking and/or separation zone comprises between about one to five vapor-liquid contacting trays.

16. The process of claim 2, wherein said upper hydrogenation and/or distillation zone comprises up to about ten fractionation trays.

17. The process of claim 1, wherein said dicyclopentadiene is fed to said catalytic distillation column through a reboiler return line.

* * * * *